United States Patent
Burns et al.

(10) Patent No.: US 6,515,153 B2
(45) Date of Patent: Feb. 4, 2003

(54) PROCESS FOR FORMING AMIDO ESTERS UTILIZING A SPINNING DISC REACTOR

(75) Inventors: Michael Eugene Burns, Hamilton, OH (US); Michael Steven Gibson, Cincinnati, OH (US); David William York, Newcastle upon Tyne (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/943,453

(22) Filed: Aug. 30, 2001

(65) Prior Publication Data

US 2002/0035281 A1 Mar. 21, 2002

(51) Int. Cl.$^7$ ............................................. C07C 231/00
(52) U.S. Cl. ........................... 554/69; 554/68; 564/123; 564/133; 564/138
(58) Field of Search ..................... 554/68, 69; 564/123, 564/133, 138

(56) References Cited

U.S. PATENT DOCUMENTS 5,523,434 A    6/1996   Burns et al.

FOREIGN PATENT DOCUMENTS

| DE | 306127 | 1/1917 |
| FR | 612315 | 7/1926 |
| WO | WO 00/48728 A1 | 8/2000 |

OTHER PUBLICATIONS

R.J. Jachuck et al., Process Intensification: The Opportunity Presented By Spinning Disc Reactor Technology, Inst. Of Chem. Eng. Symposium Series No. 141, 1997, pp 417–424.

R.J. Jachuck et al., Process Intensification: Spinning Disc Polymeriser, Inst. Of Chem. Eng. Research Event/First European Conference, 1995, pp. 556–558.

R.J. Jachuck et al., Photo–initiated Polymerisation Using Spinning Disc Reactor, 3$^{rd}$ Intern'l. Conf. On Pl, Oct. 1999, pp. 25–27.

*Primary Examiner*—Deborah D. Carr
(74) *Attorney, Agent, or Firm*—James F. McBride; Kim W. Zerby; Steven W. Miller

(57) ABSTRACT

The present invention relates to the formation of an amido ester having the formula:

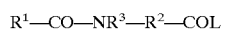

or

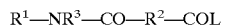

wherein $R^1$ is $C_1$–$C_{12}$ linear or branched alkyl, $C_6$–$C_{14}$ aryl, $C_7$–$C_{14}$ alkyl substituted aryl unit; $R^2$ is $C_1$–$C_{14}$ alkylene, $C_6$–$C_{14}$ arylene, $C_7$–$C_{14}$ alkyl substituted arylene; $R^3$ is hydrogen, $C_1$–$C_{10}$ alkyl, $C_6$–$C_{10}$ aryl, $C_7$–$C_{10}$ alkyl substituted aryl, L is a aryl leaving group having the formula:

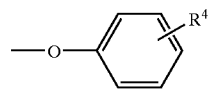

$R^4$ comprises one or more anionic or cationic units, wherein said compound is formed using a spinning disc reactor.

11 Claims, No Drawings

PROCESS FOR FORMING AMIDO ESTERS UTILIZING A SPINNING DISC REACTOR

TECHNICAL FIELD

The present invention relates to a process for forming esters and amides wherein said process is conducted using a spinning disc reactor. The invention also relates to a process for making ester and amide precursors, inter alia, acid chlorides wherein a spinning disc reactor is used in combination with reaction intermediates to increase reaction yields and purity. In addition, the present process relates to trans-esterfication reactions which can be conducted using a spinning disc reactor.

BACKGROUND OF THE INVENTION

Setting aside the ubiquity of side reactions, even the most direct organic reactions result in the need for purification, for example, removal of excess reagent, solvent. Impurities, however, are typically reaction products which have been formed by an alternate reaction pathway or can be products having an undesirable spatial orientation, therefore, in many instances, they resemble the final desired reaction product. The organic chemist seeks to ameliorate the formation of these product-like impurities by adjusting the reaction strategy, the reaction condition, inter alia, temperature, rate of addition, as well as the reactant stoichiometry. In fact, purification costs for some organic reactions may exceed the cost of raw materials.

The formation of amides and esters by the reaction of a carboxylic acid and an amine or an alcohol are two of the oldest, but most utilitarian reactions known since the amide and ester group are perhaps the most abundant of organic functional groups. Their ease of formation also makes the preparation of these functional groups highly susceptible to undesirable by-products. Peptide chemsists have dealt with the formation of amide and ester bonds for over a century and have worked out many procedures for the facile formation of amide and ester bonds in the presence of other reactive functional groups, however, many of these procedures are not applicable on either an intermediate or a large, industrial scale.

One problem faced with esters and amides is the fact the reactants, by the very nature of their own functional groups, carboxylic acids, amines, and alcohols, are more water soluble than the corresponding products. Therefore, during formation of the final product, there can be phase separations, as well as the formation of final products (esters and amides) which are more reactive than the carboxylic acid starting material. This latter case can lead to unwanted transamidation or transesterification.

Certain types of amides and esters necessarily have like reactive units, inter alia, N-acyl amino acids. In the area of bleach catalysts many of the compounds are carboxylic acids comprising an amide bond within the molecule. There is a long felt need to be able to directly form these materials without the high cost of purification or without the need to engage in several processing steps which would added cost to the final product.

It has now been surprisingly found that carboxylic acids comprising an amide functional group can be prepared by the use of a spinning disc reactor, said reactor affording a final product which has enhanced purity and yield.

SUMMARY OF THE INVENTION

The present invention meets the aforementioned need in that it has been surprisingly discovered that the use of a spinning disc reactor when conducting amide and ester forming reactions provides a reaction product having enhanced yields and reduced reaction side products.

The first aspect of the present invention relates to a process for preparing a compound having the formula:

$$R^1\text{—CO—NR}^3\text{—R}^2\text{—COOH}$$

or $$R^1\text{—NR}^3\text{—CO—R}^2\text{—COOH}$$

wherein $R^1$ is $C_1$–$C_{12}$ linear or branched alkyl, $C_6$–$C_{14}$ aryl, $C_7$–$C_{14}$ alkyl substituted aryl unit; $R^2$ is $C_1$–$C_{14}$ alkylene, $C_6$–$C_{14}$ arylene, $C_7$–$C_{14}$ alkyl substituted arylene; $R^3$ is hydrogen, $C_1$–$C_{10}$ alkyl, $C_6$–$C_{10}$ aryl, $C_7$–$C_{10}$ alkyl substituted aryl, said process comprising the steps of:

a) charging to a spinning disc reactor a carboxylic acid having the formula:

$$R^1\text{—COOH};$$

with an amine having the formula:

$$HNR^3\text{—R}^2\text{—COOH};$$

or a carboxylic acid having the formula:

$$HOOC\text{—R}^2\text{—COOH};$$

with an amine having the formula:

$$R^1\text{—NR}^3H;$$

to form an amide; and b) isolating said amide.

A further aspect of the present invention relates to a process wherein a reactive intermediate is formed, inter alia, a acid chloride prior to addtion of the amine.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference.

DETAILED DESCRIPTION OF THE INVENTION

Spinning Disc Reactor

The present invention relates to the use of a spinning disc reactor. The reactor itself may be configured in any manner which is convenient to the formulator, however, each of the one or more discs or plates rotate about an axis. The plates themselves are enclosed within a container suitable for carrying out the herein described reactions. For the purposes of the present invention, the reactants can by charged to the plate at any point along the surface, however, one embodiment relates to addition of all reactants, including solvents at the axis and allowing the centrifugal created by the rotating disc to provide a means for admixing the reactants.

Non-limiting examples of spinning disc reactors are disclosed in "Process Intensification: The opportunity presented by spinning disk reactor technology;" *Inst. of Chem. Eng. Symp. Ser.* 1997; R. Jachuck, C. Ramshaw, K. Boodhoo, and J Dalgleish, 141, 417–424; "Photo-initiated polymerisation using spinning disc reactor," Jachuck, R. J.

and Ramshaw, C., Third International Conference on PI, Antwerp 25–27 October 1999; and "Process Intensification: spinning disc polymeriser," IchemE Research Event—First European Conference for Young Researchers in Chemical Engineering.

The speed of rotation of the disc and the rate at which the reactants are introduced ontot the disc can be modified by the formulator to meet the requirements of the process. For example, depending upon the time necessary for the reaction be complete, the viscosity of the reactant admixture, the rotational velocity can be adjusted to shorten or lengthen the resonance time of the reactants on each plate. In one embodiment, the plates have a velocity in acess of 100 revolution per minute (rpm), while another embodiment relates to speeds of from 1000 rpm to 2000 rpm. Depending upon the size of the rotating plates and the rotational velocity, resonance times are from 1 second to 15 seconds. Another embodiment employs resonace times of from about 2 to about 10 seconds.

The process of the present invention can be conducted at any temperature within the operable limits of the spinning disc reactor. For exothermic reactions, the apparatus is cooled within a range of from about 0° C. to about 50° C.

The following is a description of the process of the present invention.

Step (a)

Step (a) of the process of the present invention relates to formation of an amide bond by reacting a carboxylic acid having the formula:

with an amine having the formula:

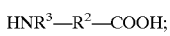

to form an amide having the formula:

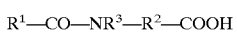

or a carboxylic acid having the formula:

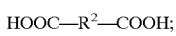

with an amine having the formula:

to form an amide having the formula:

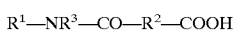

wherein $R^1$ is $C_1$–$C_{12}$ linear or branched alkyl, $C_6$–$C_{14}$ aryl, $C_7$–$C_{14}$ alkyl substituted aryl unit; $R^2$ is $C_1$–$C_{14}$ alkylene, $C_6$–$C_{14}$ arylene, $C_7$–$C_{14}$ alkyl substituted arylene; $R^3$ is hydrogen, $C_1$–$C_{10}$ alkyl, $C_6$–$C_{10}$ aryl, $C_7$–$C_{10}$ alkyl substituted aryl.

Either of the starting materials can be dissolved in a suitable solvent, non-limiting examples of which include tetrahydrofuran, dimethylformamide, methylene chloride, benzene, toluene, and the like, provided said solvent does not react with either the amine, the carboxylic acid, or the final product.

Another aspect of the present invention relates to a second class of reactions which is suitably conducted under the conditions of the present invention. This second class of reactions comprises the step of reacting an amido carboxylic acid having the formula:

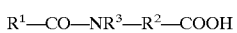

or

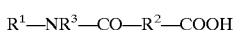

with an alcohol to form an amido ester.

One embodiment of this aspect relates to forming amido esters wherein said ester portion is a suitable leaving group under the conditions wherein said amido esters can function as peroxyacid precursors. Non-limiting examples of amido esters of this type have the formula:

or

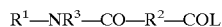

wherein $R^1$, $R^2$, and $R^3$ are the same as defined herein above, an L is a aryl leaving group having the formula:

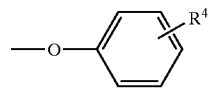

wherein $R^4$ comprises one or more anionic or cationic units which substitute the aryl ring in place of hydrogen and are present to enhance the water solubility of the resulting amido ester. $R^4$ units, in one embodiment, are 4-sulfo units resulting in $R^4$ having the formula:

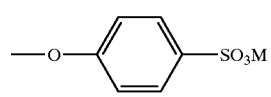

wherein M is hydrogen or a water soluble cation. The amido esters having this formula can be prepared in high yield and purity by the process of the present invention.

A further aspect of the present invention which makes use of the spinning disc reactor is the preparation of amido esters wherein an intermediate is used. In one embodiment, the intermediate is an activated carboxyl group, inter alia, the acid chloride, tosylate, and mixed anhydride. In one embodiment of this aspect, the parent carboxylic acid, having the formula:

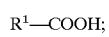

or

is reacted with a sufficient amount of a reagent to form the acid chloride. The process of the present invention is adaptable to any acylation reaction conditions, including Schotten-Baumann and the like.

This embodiment can be further extended to the formation of esters which comprise the aryl leaving group, which can thereby be formed, for example, by way of an intermediate acid chloride having the formula:

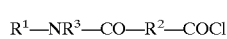

or

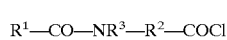

wherein said acid chloride is reacted with an alcohol to form the product amido ester. Suitable reagents for forming the acid chlorides of the present invention include thionyl chloride and oxalyl chloride. In the case wherein the dicarboxylic acid is used, the formulator will adjust the stoichiometry to allow for the mixed acid/acid chloride to form.

The present invention further relates to the use of a leaving group for use as an synthetic intermediate. One embodiment of this aspect includes the use of transesterification. Amido esters are formed wherein the alcohol used is a short chain, labile adduct, for example, methanol or other volatile or easily removable choice. Non-limiting examples of alcohols useful in the transesterification aspect of the present invention includes $C_1$–$C_{10}$ linear alkyl, and mixtures thereof.

Other aspects of the present invention include the formation of mixed anhydrides and the like as amido ester reaction intermediates.

Step (b)

Step (b) relates to isolating the product of Step (a) and includes such processes as removal of the solvent in vacuo. For high yield reactions wherein the product precipitates or crystallizes upon cooling, Step (b) may comprise nothing other than collecting the material as it is discharged from the rotating plates or discs.

EXAMPLE 1

A solution of N-nonanoyl-6-aminocaproic acid in diethylether is introduced onto the disc of the spinning disc reactor through a pipe directly above the centre of a disc, having a rotation speed of 1500 rpm. Simultaneously, through another pipe, thionlychloride is introduced onto the centre of the disc of the spinning disc reactor.

The flow rate of both reagents is adjusted to ensure a 1:1 molar ratio at the centre of the disc and a residence time of the mixture of reagents and reaction product on the disc of about 5 seconds. The disc and the reactor are cooled to ensure a temperature between 10° C. and 25° C. The resulting product is lead from the edge of the disc to a vessel under the disc, from where it is collected for further processing (including optional purification and analysis).

In a second step, the N-nonanoyl-6-aminocaproic acid chloride is dissolved in diethylether and introduced onto a disc as above; also an aqueous solution of sodium phenolsulphonate, having a pH of 9 by introduction of sodium hydroxide, is introduced onto the disc as above. Again, the flow rate of both reagents is adjusted to ensure a 1:1 molar ratio at the centre of the disc and a residence time of the mixture of reagents and reaction product on the disc of about 5 seconds. The disc and the reactor are cooled to ensure a temperature between 10° C. and 25° C. The resulting product is lead from the edge of the disc to a vessel under the disc and collected from the vessel for further processing (including optional purification and analysis).

What is claimed is:

1. A process for preparing an amido ester having the formula:

$R^1$—CO—NR$^3$—R$^2$—COOH or $R^1$—NR$^3$—CO—R$^2$—COOH wherein $R^1$ is $C_1$–$C_{12}$ linear or branched alkyl, $C_6$–$C_{14}$ aryl, $C_7$–$C_{14}$ alkyl substituted aryl unit; $R^2$ is $C_1$–$C_{14}$ alkylene, $C_6$–$C_{14}$ arylene, $C_7$–$C_{14}$ alkyl substituted arylene; $R^3$ is hydrogen, $C_1$–$C_{10}$ alkyl, $C_6$–$C_{10}$ aryl, $C_7$–$C_{10}$ alkyl substituted aryl, said process comprising the steps of:

a) charging to a spinning disc reactor a carboxylic acid having the formula:

$R^1$—COOH;

with an amine having the formula:

HNR$^3$—R$^2$—COOH;

or a carboxylic acid having the formula:

HOOC—R$^2$—COOH;

with an amine having the formula:

$R^1$—NR$^3$H;

to form an amido ester; and
b) isolating said amido ester.

2. A process according to claim 1 wherein $R^1$ is $C_9$ linear alkyl.

3. A process according to claim 1 wherein $R^2$ is $C_6$ linear alkylene.

4. A process according to claim 1 wherein $R^3$ is hydrogen.

5. A process according to claim 1 further comprising the step of forming an intermediate acid chloride having the formula:

$R^1$—COCl or

HOOC—R$^2$—COCl prior to adding said amine.

6. A process for preparing an amido ester having the formula:

$R^1$—CO—NR$^3$—R$^2$—COL or $R^1$—NR$^3$—CO—R$^2$—COL wherein $R^1$ is $C_1$–$C_{12}$ linear or branched alkyl, $C_6$–$C_{14}$ aryl, $C_7$–$C_{14}$ alkyl substituted aryl unit; $R^2$ is $C_1$–$C_{14}$ alkylene, $C_6$–$C_{14}$ arylene, $C_7$–$C_{14}$ alkyl substituted arylene; $R^3$ is hydrogen, $C_1$–$C_{10}$ alkyl, $C_6$–$C_{10}$ aryl, $C_7$–$C_{10}$ alkyl substituted aryl, L is a aryl leaving group having the formula:

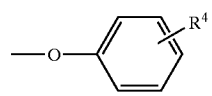

$R^4$ comprises one or more anionic or cationic units, said process comprising the steps of:

a) charging to a spinning disc reactor a carboxylic acid having the formula:

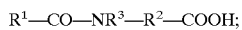

or the formula:

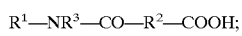

with an alcohol having the formula:

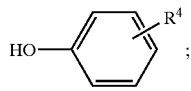

to form an amido ester; and
b) isolating said amido ester.

7. A process according to claim 6 wherein $R^1$ is $C_9$ linear alkyl.

8. A process according to claim 6 wherein $R^2$ is $C_6$ linear alkylene.

9. A process according to claim 6 wherein $R^3$ is hydrogen.

10. A process according to claim 6 wherein L has the formula:

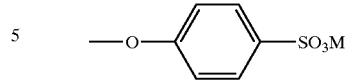

11. A process according to claim 6 further comprising the step of forming an intermediate acid chloride having the formula:

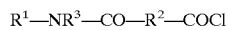

or

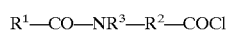

prior to adding said amine.

* * * * *